US009451952B2

(12) United States Patent
Ostrovsky et al.

(10) Patent No.: US 9,451,952 B2
(45) Date of Patent: Sep. 27, 2016

(54) SUTURING DEVICE

(71) Applicant: BOSTON SCIENTIFIC SCIMED, INC., Maple Grove, MN (US)

(72) Inventors: Isaac Ostrovsky, Wellesley, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 229 days.

(21) Appl. No.: 13/794,053

(22) Filed: Mar. 11, 2013

(65) Prior Publication Data

US 2013/0253542 A1    Sep. 26, 2013

Related U.S. Application Data

(60) Provisional application No. 61/614,138, filed on Mar. 22, 2012.

(51) Int. Cl.
| | |
|---|---|
| *A61B 17/04* | (2006.01) |
| *A61B 17/062* | (2006.01) |
| *A61B 17/06* | (2006.01) |
| *A61F 2/00* | (2006.01) |

(52) U.S. Cl.
CPC ....... *A61B 17/0491* (2013.01); *A61B 17/0482* (2013.01); *A61B 17/062* (2013.01); *A61B 17/0469* (2013.01); *A61B 17/0483* (2013.01); *A61B 17/0485* (2013.01); *A61B 2017/06042* (2013.01); *A61F 2/0045* (2013.01)

(58) Field of Classification Search
CPC .......... A61B 17/0482; A61B 17/0491; A61B 17/062; A61B 17/0469; A61B 17/0483; A61B 17/0485; A61B 2017/06042; A61B 17/0625; A61B 2017/047; A61F 2/0045
See application file for complete search history.

(56) References Cited

U.S. PATENT DOCUMENTS

| | | | |
|---|---|---|---|
| 4,312,337 A | | 1/1982 | Donohue |
| 5,059,207 A | * | 10/1991 | Shah ................ A61B 17/06066 223/102 |

(Continued)

FOREIGN PATENT DOCUMENTS

| | | |
|---|---|---|
| EP | 0941698 A1 | 9/1999 |
| EP | 2033583 A1 | 3/2009 |

(Continued)

OTHER PUBLICATIONS

International Search Report and Written Opinion for PCT Patent Application No. PCT/US2013/055097, mailed on Dec. 3, 2013, 11 pages.

(Continued)

*Primary Examiner* — Thomas McEvoy
(74) *Attorney, Agent, or Firm* — Brake Hughes Bellermann LLP

(57) ABSTRACT

In some embodiments, the present invention discloses a suturing device including an elongate member having a head portion, a tail portion and a needle receiving portion provided on the head portion. The needle receiving portion has a recess that is configured to receive a suture and hold it within the recess. The needle receiving portion is fixed with respect to an opening defined at the head portion. The suturing device further includes a needle having a retracted state and a deployed state. The needle includes a needle notch at a distal portion of the needle. The needle is configured to enter the recess of the needle receiving portion and receive the suture within the needle notch.

15 Claims, 18 Drawing Sheets

(56) References Cited

U.S. PATENT DOCUMENTS

| | | | |
|---|---|---|---|
| 5,474,568 A | 12/1995 | Scott | |
| 5,782,866 A * | 7/1998 | Wenstrom, Jr. | A61B 17/0401 606/232 |
| 6,048,351 A | 4/2000 | Gordon et al. | |
| 6,475,135 B1 * | 11/2002 | Levy | A61B 17/0469 128/885 |
| 6,551,330 B1 | 4/2003 | Bain et al. | |
| 6,955,643 B2 | 10/2005 | Gellman et al. | |
| 2003/0078599 A1 | 4/2003 | O'Quinn et al. | |
| 2004/0015177 A1 | 1/2004 | Chu | |
| 2004/0138682 A1 | 7/2004 | Onuki et al. | |
| 2005/0015101 A1 | 1/2005 | Gibbens et al. | |
| 2006/0195121 A1 | 8/2006 | Chu | |
| 2006/0282094 A1 | 12/2006 | Stokes et al. | |
| 2007/0270885 A1 | 11/2007 | Weinert et al. | |
| 2009/0131956 A1 | 5/2009 | Dewey et al. | |
| 2009/0171143 A1 | 7/2009 | Chu et al. | |
| 2009/0312772 A1 | 12/2009 | Chu | |
| 2011/0022063 A1 | 1/2011 | McClurg et al. | |
| 2011/0066165 A1 * | 3/2011 | Skinlo | A61B 17/0469 606/145 |
| 2014/0052159 A1 | 2/2014 | Teague et al. | |

FOREIGN PATENT DOCUMENTS

| | | |
|---|---|---|
| WO | 2008/030893 A2 | 3/2008 |
| WO | 2011/008607 A1 | 1/2011 |
| WO | 2013/142680 A1 | 9/2013 |
| WO | 2014/028710 A1 | 2/2014 |

OTHER PUBLICATIONS

International Preliminary Report on Patentability for PCT Patent Application No. PCT/US2013/033290, mailed on Oct. 2, 2014, 10 pages.

International Search Report and Written Opinion for PCT Patent Application No. PCT/US2013/033290, mailed on Jun. 25, 2013, 15 pages.

Bard Medical, "FIXT Suturing Device", C.R. Bard, Inc., 2011, 4 pages.

Bard Medical, "FIXT iPhone Book", C.R. Bard, Inc., 2011, 8 pages.

Lazarou, George, "Vaginal Prolapse", eMedicineHealth.com, 2014, 3 pages.

Non-Final Office Action for U.S. Appl. No. 13/966,767, mailed on Dec. 16, 2015, 15 pages.

Non-Final Office Action Response for U.S. Appl. No. 13/966,767, filed Mar. 14, 2016, 9 pages.

* cited by examiner

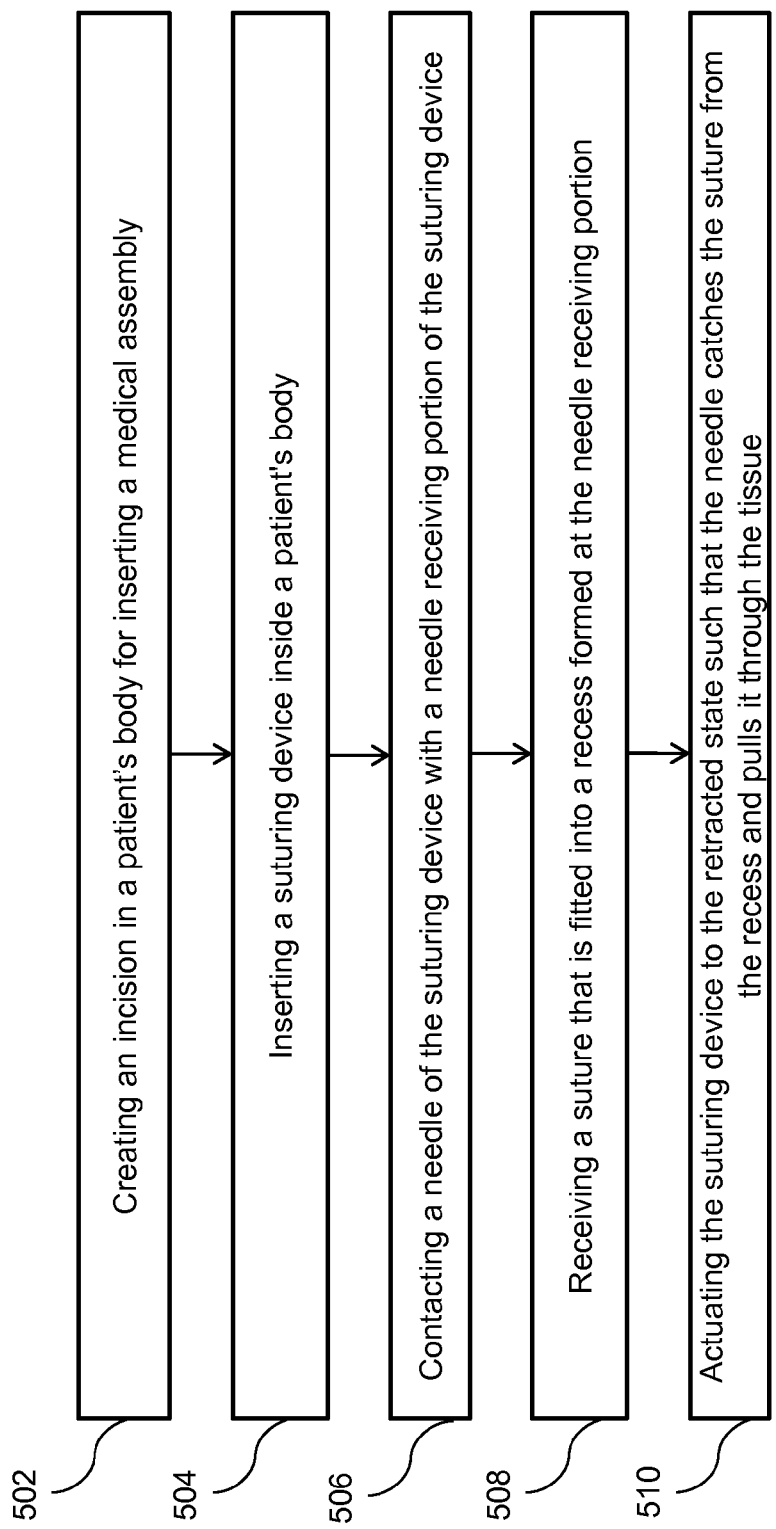

SUTURING DEVICE

CROSS-REFERENCE TO RELATED APPLICATION

This application is a Nonprovisional of, and claims priority to, U.S. Patent Application No. 61/614,138, filed Mar. 22, 2012, entitled "A SUTURING DEVICE", which is incorporated by reference herein in its entirety.

BACKGROUND

1. Field

The present invention generally relates to surgical devices and procedures, particularly to devices and methods for the delivery of sutures and implants with sutures within a patient's body.

2. Description of the Related Art

Suturing of body tissues is a time consuming and an important aspect of most surgical procedures. Many surgical procedures are performed where it is necessary to make a large opening to expose an area of, for instance, a bodily tissue of a human body that requires a surgical repair. In various corrective surgeries or implant procedures, the bodily tissue must be returned to a normal anatomical position or placed in an improved position.

Suturing devices are used for these types of surgeries. These devices work on the mechanism of driving a needle loaded with a suture through a bodily tissue to be sutured and catching the needle after the suture has been placed. These needles loaded with a suture are specifically made for this process. Such devices include a needle catch portion and a needle catch slot provided in the needle catch portion to catch the needle.

The existing suturing mechanisms and devices may require pre-fabricated customized needles that are compatible to be used in these suturing devices. One may need to stock these types of needles for an unexpected use. The suture loaded needles may be relatively expensive as compared to sutures. Also, it may be difficult to load the suture loaded needles onto the suturing device and the needles may come off from the sutures due to occurrence of any manufacturing process imperfection. This may make the suturing process less cost-effective and dependent on the manufacturing quality of the needle loaded with the suture.

In view of the above, there is a need for a device and a method which could operate with normal sutures and could also circumvent the action of loading the needles onto the device.

SUMMARY

In some embodiments, the present invention discloses a suturing device including an elongate member having a head portion, a tail portion and a needle receiving portion provided on the head portion. The needle receiving portion has a recess that is configured to receive a suture and hold it within the recess. The needle receiving portion is fixed with respect to an opening defined at the head portion. The suturing device further includes a needle having a retracted state and a deployed state. The needle includes a needle notch at a distal portion of the needle. The needle is configured to enter the recess of the needle receiving portion and receive the suture within the needle notch.

In some embodiments, the invention discloses a suturing device having an elongate member having a head portion, a tail portion and a needle receiving portion provided on the head portion. The needle receiving portion has a recess. The recess is configured to receive a suture. The needle receiving portion is fixed with respect to an opening defined at the head portion. The elongate member includes a lumen along a length of the elongate member. The suturing device further includes a needle deployment mechanism disposed at least partially within the lumen of the elongate member. The needle deployment mechanism includes an actuator at least partially disposed within the lumen of the elongate member and a curved needle coupled to the actuator. The curved needle is provided with a needle notch at a distal portion. The curved needle is configured to at least partially exit the lumen in a deployed state and is completely contained inside the lumen in a retracted state of the suturing device. The distal portion of the curved needle is configured to enter the recess of the needle receiving portion and receive the suture within the needle notch while in a retracted state.

In some embodiments, the invention discloses a method for suturing a tissue. The method includes inserting a suturing device having an elongate member inside a patient's body for suturing the tissue. The suturing device is in a retracted state during insertion. The method further includes contacting a needle of the suturing device with a needle receiving portion of the suturing device by actuating the suturing device to a deployed state. The needle includes a needle notch at a distal portion. The needle receiving portion extends at a head portion of the elongate member. The needle receiving portion is fixed with respect to an opening of the elongate member. The method further includes receiving a suture that is fitted into a recess formed at the needle receiving portion. The method also includes actuating the suturing device to the retracted state such that the needle catches the suture from the recess and pulls the suture through the tissue.

BRIEF DESCRIPTION OF THE FIGURES

The invention and the following detailed description of certain embodiments thereof may be understood with reference to the following figures:

FIG. 5 illustrates a flowchart representing a method for delivery of a suture in a patient's body in accordance with an embodiment of the present invention.

DETAILED DESCRIPTION

Figure 1:
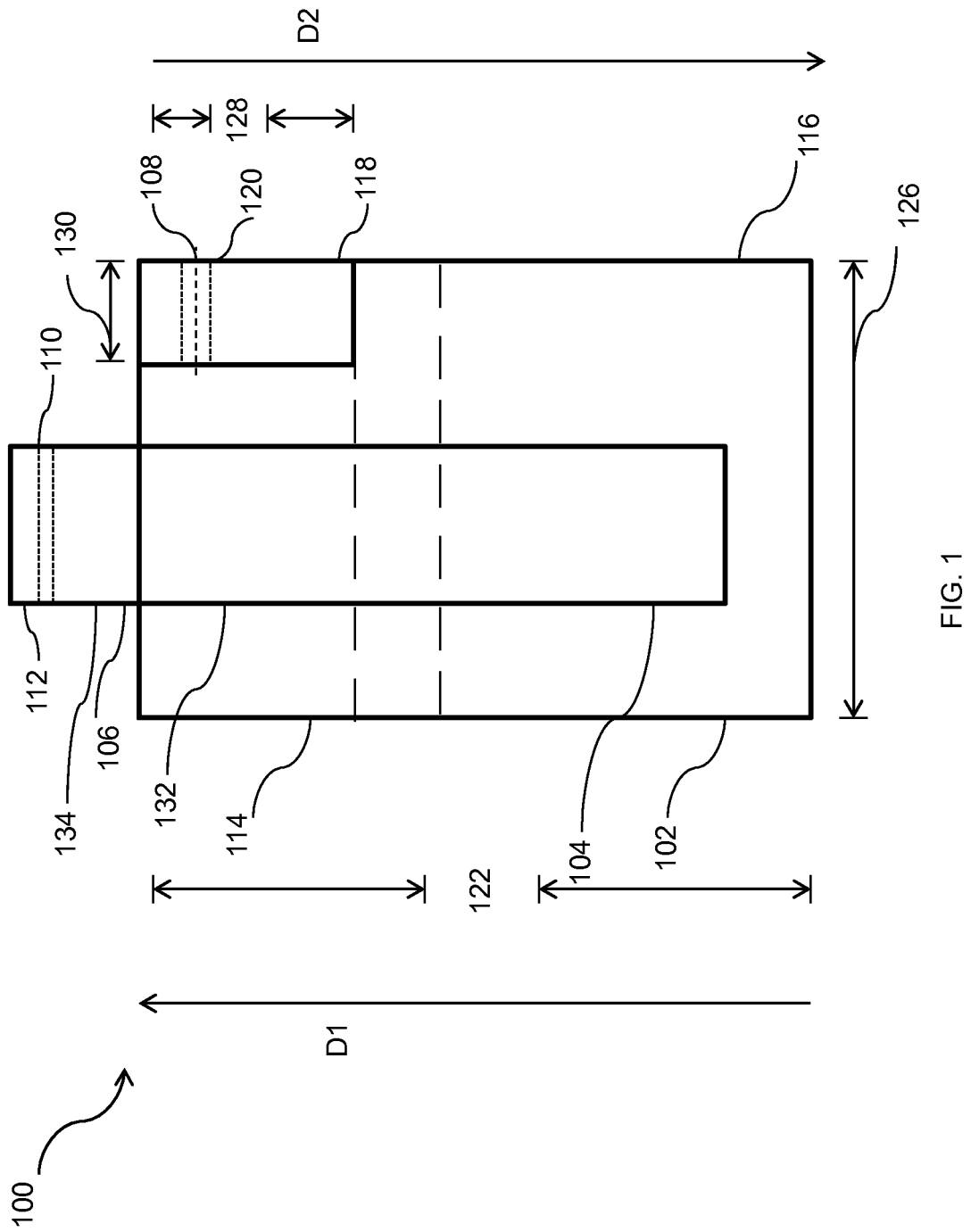
FIG. 1 is a schematic diagram of a suturing device, in accordance with some embodiments of the present invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The terms "a" or "an," as used herein, are defined as one or more than one. The term "another," as used herein, is defined as at least a second or more. The terms "including" and/or "having", as used herein, are defined as comprising (i.e., open transition).

The terms proximal and distal described in relation to various medical devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure of surgery through the patient's body orifice as described in the present invention. The term proximal refers to an area that is closest to the operator. The term distal refers to an area that is farthest from the operator. The patient can be a male, a female or any other mammal.

The devices and methods described herein are generally directed to insertion and delivery tools for placing sutures within a body of a patient. The sutures delivered using such an insertion and delivery tool may be used in any portion of the body of the patient. In some embodiments, the sutures include, but are not limited to be placed within a pelvic region of a patient. In some embodiments, the insertion and delivery tool may be a suturing device that can be used for placing sutures inside the pelvic region of the body of the patient.

The suturing device may be inserted within the pelvic region of the patient and sutures can be secured at any of the several locations within the pelvic region to fix an implant for the treatment of pelvic dysfunctions. For example, the implant can be secured to a sacrospinous ligament or a ureterosacral ligament for uterine preservation. In yet another embodiment, the suture can be secured to a sacrospinous ligament or an arcus tendineus fascia pelvis (i.e., white line) (also referred to herein as "arcus tendineus") for paravaginal repairs including, for example, cystoceles, rectoceles and enteroceles. A suture can also be secured to various of such locations. The suturing devices and procedures described herein may be used in a female patient and/or a male patient.

In some embodiments, the disclosed suturing device may be used to place the implant, for example, through a vaginal incision, in a retro-pubic direction (behind the pubic bone), or in a pre-pubic direction (in front of the pubic bone). In other embodiments, the implant can be placed to target other anatomical structures or tissues as desired. Various embodiments of suturing device are described herein. The suturing device may be used to deliver sutures at different tissues into the body of a patient and only some examples of the tissues are described herein.

FIG. 1 is a schematic diagram of a suturing device 100, in accordance with some embodiments of the present invention. The suturing device 100 includes an elongate member 102, a needle deployment mechanism 104, and a needle 106. In some embodiments, the suturing device 100 is configured to place a suture 108 across a bodily tissue for the treatment of pelvic floor disorders or any other disorder. In accordance with various embodiments, the suturing device 100 may be used to insert various types of implants into the body of the patient. In some embodiments, the suturing device 100 can be configured to place the suture 108 into a pelvic region of the patient.

The elongate member 102 of the suturing device 100 includes a head portion 114, a tail portion 116 and a needle receiving portion 118 provided on the head portion 114. The elongate member 102 further defines an opening at the head portion 114. The needle receiving portion 118 is fixed with respect to the opening of the elongate member 102. A length 122 of the elongate member 102 extends between the tail portion 116 and the head portion 114 longitudinally.

In some embodiments, the elongate member 102 includes a lumen extending from the head portion 114 to the tail portion 116 of the elongate member 102. The lumen of the elongate member 102 is configured to receive and house at least some elements and portions of the suturing device 100. For example, the lumen can house at least some portion of the needle deployment mechanism 104 within a space formed within the lumen.

The elongate member may further be coupled to a handle. The handle is provided on the tail portion of the elongate member. In some embodiments, the handle of the suturing device may be configured to assist the operator of the suturing device 100 in holding the suturing device 100.

In some embodiments, the head portion 114 of the elongate member 102 has a tip portion. In some embodiments, the tip portion may be tapered. The tip portion may be configured to slide through a bodily tissue and facilitate an insertion and movement through the patient's body. In accordance with some embodiments of the invention, the head portion 114 of the elongate member 102 may include a curved portion (not shown).

The head portion 114 of the elongate member 102 includes the needle receiving portion 118. As discussed above, the needle receiving portion 118 is fixed with respect to the opening of the elongate member 102. The needle receiving portion 118 includes a recess 120 (discussed later).

In accordance with some embodiments of the invention, the needle receiving portion 118 of the suturing device 100 can have a length 128 as shown in FIG. 1. The length 128 can vary based on the requirements. For example, in some embodiments, the length 128 can vary from 0.30 inch to 0.50 inch. In some embodiments, the length 128 can be 0.40 inch. In some embodiments of the invention, the needle receiving portion can have a width 130 as shown in FIG. 1. The width 130 can vary based on the requirements. For example in some embodiments, the width 130 can vary from 0.200 inch to 0.220 inch. In some embodiments the width 130 can be 0.210 inch.

In some embodiments, the needle receiving portion 118 can have a height (not visible in FIG. 1 and is explained later) that can vary based on requirements. In some embodiments, the height of the needle receiving portion 118 can be different at different portions. For example, in some embodiments, the height along at first portion can vary from 0.140 inch to 0.0160 inch and the height at a second portion can vary from 0.040 inch to 0.060 inch. In some embodiments, the height of the needle receiving portion 118 can be same at all portions.

As mentioned above, the needle receiving portion 118 includes or defines a recess 120. In various embodiments, the recess 120 can be in the form of a slot, an aperture, an opening, or any other type of a hollow space on the needle receiving portion 118 such that the recess is configured to receive the suture. In some embodiments, the recess 120 is configured to hold the suture within the hollow space provided by the recess, such as via a frictional or compression fit. In some embodiments, the recess 120 can be, for example, an L-shaped slot or a T-shaped slot. In accordance with several embodiments, the holding force between the suture and the needle receiving portion that is capable of holding the suture within the recess may be generated through various modes. In an embodiment, for example, the required holding force may be generated through a compress fit method of inserting the suture within the recess. In accordance with this embodiment, the recess 120 of the needle receiving portion has a dimension smaller than an outer diameter of the suture 108. This difference in dimension allows the suture 108 to compress fit within the recess 120. In some embodiments of the invention, at least a portion of an implant (not shown) configured to be inserted into a body of a patient can be coupled to the suture 108. In several other embodiments, the holding force can be generated by various modes other than compress fitting. In some embodiments, the suture 108 can be placed into the recess 120 by applying a push force to the suture 108 so that it compress fits into the recess. In such cases, the dimension of the recess 120 and the outer diameter of the suture 108 can be equal or the dimension of the recess can be even more than the diameter of the suture. In accordance with these embodiments, the suture may be coupled to the recess through various other means that may temporarily hold the suture firmly. In other embodiments, the recess 120 is configured to retain the suture in place via a frictional fit between the suture and the needle receiving portion 118.

The suturing device 100 further includes a needle deployment mechanism 104. The needle deployment mechanism 104 is disposed at least partially within the elongate member 102. The needle deployment mechanism 104 is configured to provide either of a deployed state or a retracted state to the suturing device. In some embodiments, the needle deployment mechanism 104 is coupled to the elongate member 102 at the tail portion 116. In some embodiments, the needle deployment mechanism 104 is at least partially disposed within the lumen of the elongate member 102. In some embodiments, the needle deployment mechanism 104 includes an actuator at least partially disposed within the lumen of the elongate member 102. In some embodiments of the invention, the actuator provides the deployed state and the retracted state to the suturing device.

In some embodiments, the actuator can be actuated between the deployed state and the retracted state through a button. The button can be provided on the tail portion of the elongate member or on the handle in accordance with different embodiments.

The suturing device can be moved from the retracted state to the deployed state by actuating the needle deployment mechanism along a direction D1. After being moved to the deployed state, the needle deployment mechanism can be moved to the retracted state by actuating the needle deployment mechanism along a direction D2 which is opposite to the direction D1. In some embodiments, the needle deployment mechanism is biased to its retracted state.

The suturing device 100 further includes the needle 106. The needle 106 of the suturing device is coupled to a distal portion 132 of the needle deployment mechanism 104. The needle 106 includes the needle notch 110 at a distal portion 112 of the needle. The needle 106 is connected to the needle deployment mechanism 104 of the suturing device 100. The needle 106 is configured to enter the recess 120 of the needle receiving portion 118 and receive the suture 108 within the needle notch 110 while in the retracted state.

In some embodiments, the needle 106 can be coupled to the actuator of the needle deployment mechanism 104 at a distal end of the actuator. In some embodiments, the distal end of the actuator is same as the distal end 132 of the needle deployment mechanism 104.

In some embodiments, the needle 106 has a substantially circular cross section. In some embodiments of the invention, the needle 106 is a curved needle. In some embodiments, the needle 106 can have a shape different than a circular cross-sectional shape. In some embodiments, the needle 106 can have a cross-sectional shape (or outer shape) of any type of polygon. For example, the needle 106 can have a square or a rectangular cross-sectional shape (or outer profile). In some embodiments, the needle 106 can have a tapered shape and/or a tapered portion (e.g., tapered from a proximal portion 134 to a distal portion 112). In such embodiments, the needle 106 can have a varying diameter or width.

In some embodiment, the needle 106 is at least partially disposed into the lumen of the elongate member 102 of the suturing device 100. The needle is configured to at least partially exit the lumen in the deployed state and may be completely contained inside the lumen in the retracted state of the suturing device 100.

In some embodiments, at least a portion of the needle 106 can be formed of a flexible material. For example, a portion of the needle 106 that remains disposed within the lumen when the suturing device 100 is in the retracted state can be configured to flex or bend. In some embodiments, at least a portion of the needle 106 can be formed of the flexible material so that the portion of the needle 106 can conform to a curvature of the lumen, as the needle 106 is slidably moved within the lumen.

In some embodiments, the needle notch 110 includes a beveled edge (also referred to as needle bevel). The needle notch 110 of the needle 106 is configured to pick up the suture 108 from the recess 120 of the needle receiving portion 118 in order to place the suture 108 through the bodily tissues. Also, the suture 108 jammed into the recess 120 of the needle receiving portion 118 can be a usually used suture or customized suture.

In accordance with some embodiments of the invention, when the suturing device 100 is in the retracted state, the distal end 112 of the needle 106 can be disposed within the lumen of the elongate member 102. When the suturing device 100 moves to the deployed state, the distal end 112 of the needle 106 followed by the proximal end 134 of the needle 106, start moving out of the lumen and toward the recess 120 of the needle receiving portion 118. When the suturing device 100 reaches the deployed state, the needle 106 is completely or substantially extended out of the lumen, has pushed through the bodily tissue and entered into the recess 120 of the needle receiving portion 118.

In some embodiments, when the suturing device 100 is moved to the deployed state, the needle notch 110 of the needle 106 can receive the suture placed in the recess 120 of the needle receiving portion 118. When the suturing device 100 is moved to the refracted state after needle notch 120 receives the suture 108, the suture 108 can be extracted or removed from the recess 120 of the needle receiving portion 118. The suture 108 along with the needle 106 is moved away from the needle receiving portion 118 and toward the lumen of the elongate member 102 as the suturing device 100 is moved to the retracted state. In accordance with the embodiments of the invention, the suture 108 has two ends such that one end is configured to completely pass through the bodily tissues upon retraction and reside on an opposite side. The length of the suture portion that is configured to pass across the bodily tissue to the opposite side may be 8-15 centimeter (8-15 cm), in some embodiments. In some embodiments, this length of the suture portion is at least equal to width of the tissue or opening that is configured to be sutured. In some embodiments, the suture 108 is placed in the recess 120 in such a way that one of the ends of the suture is at a distance of 8-15 centimeter (8-15 cm) from the recess 120 so that the suture 108 leaves suture portions on both sides of the recess 120. The distance of 8-15 cm on one end makes one of the suture portions at one side of the recess shorter than the other. When the needle is retracted back to the lumen of the elongate member 102 of the suturing device 100, the suture portions also get pulled along with the needle into the lumen of the elongate member 102 through the tissues. When the suture 216 is pulled through, the short suture portion completely passes through the bodily tissue and resides on the opposite side.

FIGS. 2A-2E illustrate and elaborate various structural components of a suturing device 200, in accordance with some embodiments.

Figure 2A:
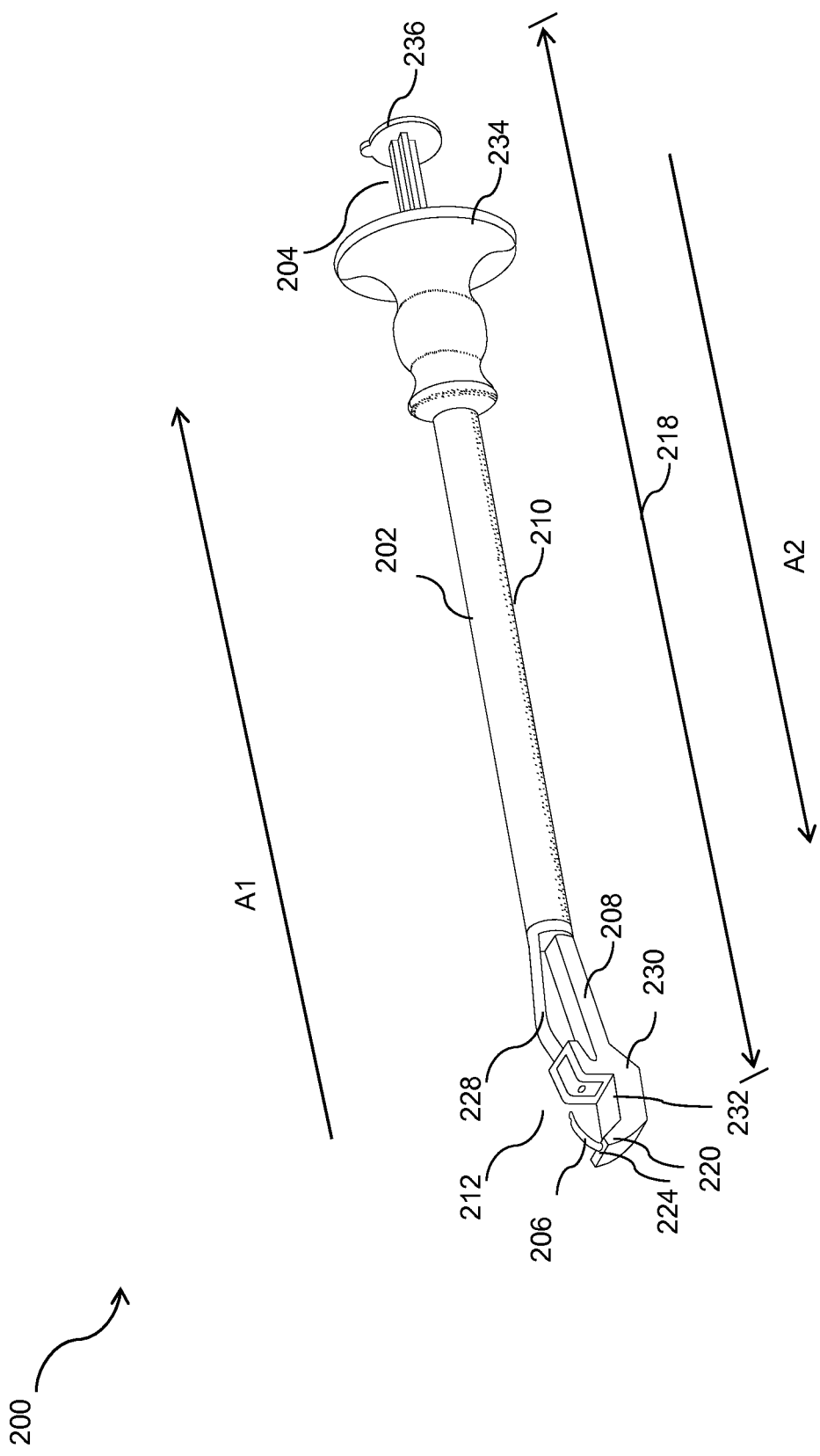
FIG. 2A is a perspective view of a suturing device, in accordance with an embodiment of the present invention.
Figure 2B:
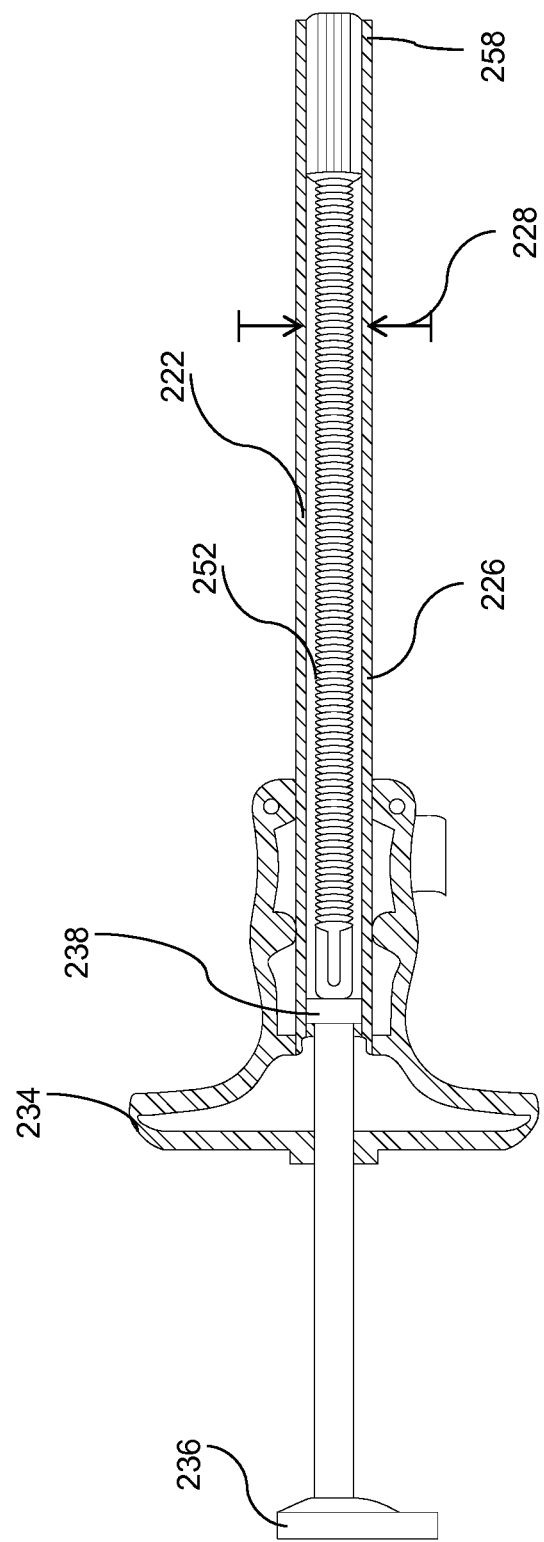
FIG. 2B is a cross-sectional view of a portion of the suturing device of FIG. 2A.

Referring now to FIGS. 2A and 2B, the suturing device 200 is described. FIG. 2A is a perspective view of the suturing device 200, in accordance with some embodiments of the present invention. FIG. 2B illustrates a cross-sectional view of a portion of the suturing device 200, in accordance with some embodiments of the invention. The suturing device 200 includes an elongate member 202, a needle deployment mechanism 204 and a needle 206. The needle deployment mechanism 204 is at least partially disposed within the elongate member 202.

The elongate member 202 of the suturing device 200 includes a head portion 208, a tail portion 210 and a needle receiving portion 212 provided on the head portion 208. The elongate member 202 further defines an opening at the head portion 208. The needle receiving portion 212 is fixed with respect to the opening 224 of the elongate member 202. A length 218 of the elongate member 202 extends between the tail portion 210 and the head portion 208 longitudinally.

The tail portion 210 of the elongate member 202 is configured to receive and house at least some other elements and portions of the suturing device 200. For example, the tail portion 210 can be configured to house at least some portion of a handle 234 of the suturing device 200. The handle may be configured to assist the operator of the suturing device 200 in holding the suturing device 200.

In some embodiments of invention, the tail portion 210 of the elongate member 202 houses a bearing 238 (illustrated in FIG. 2B) that is configured to act as a coupling bridge between the elongate member 202 of the suturing device 200 and the needle deployment mechanism 204 of the suturing device 200.

In some embodiments, the head portion 208 of the elongate member 202 includes a lumen 222 extending from the head portion 208 to the tail portion 210 of the elongate member 202. The lumen 222 is defined along the inner walls of the elongate member 202. In some embodiments, the inner walls of the elongate member 202 define a cylindrical profile 226. An inner diameter of the elongate member across the inner walls is represented by 228. In some embodiments, the profile defined by the inner walls can be similar to a polygon, a square, a rectangle, trapezoid, cylindrical. The lumen 222 of the elongate member 202 is configured to receive and house at least some other elements and portions of the suturing device 200. For example, the elongate member 202 can be configured to house at least some portion of the needle deployment mechanism 204 within a space formed within the lumen 222. In some embodiments, the needle 206 is at least partially disposed into the lumen 222.

The head portion 208 includes a tip portion 220. The tip portion may be tapered. In some embodiments, the tip portion 220 is configured to slide through a bodily tissue and facilitate an insertion and movement through the patient's body. The tip portion defines an opening 224 at a distal end of the head portion 208. The head portion 208 of the elongate member 202 includes the needle receiving portion 212 of the suturing device 200.

In accordance with some embodiments of the invention, the head portion 208 of the elongate member 202 includes a protuberance 228 and a curved portion 230. The curved portion 230 defines a second opening 232 for receiving a tissue. The lumen 222 of the elongate member 202 extends through the curved portion 230 and abuts at the opening 224 of the head portion 208 of the elongate member 202.

The head portion 208 of the elongate member 202 includes the needle receiving portion 212. As discussed above, the needle receiving portion 212 is fixed with respect to the opening 224 of the elongate member 202.

Figure 2C:
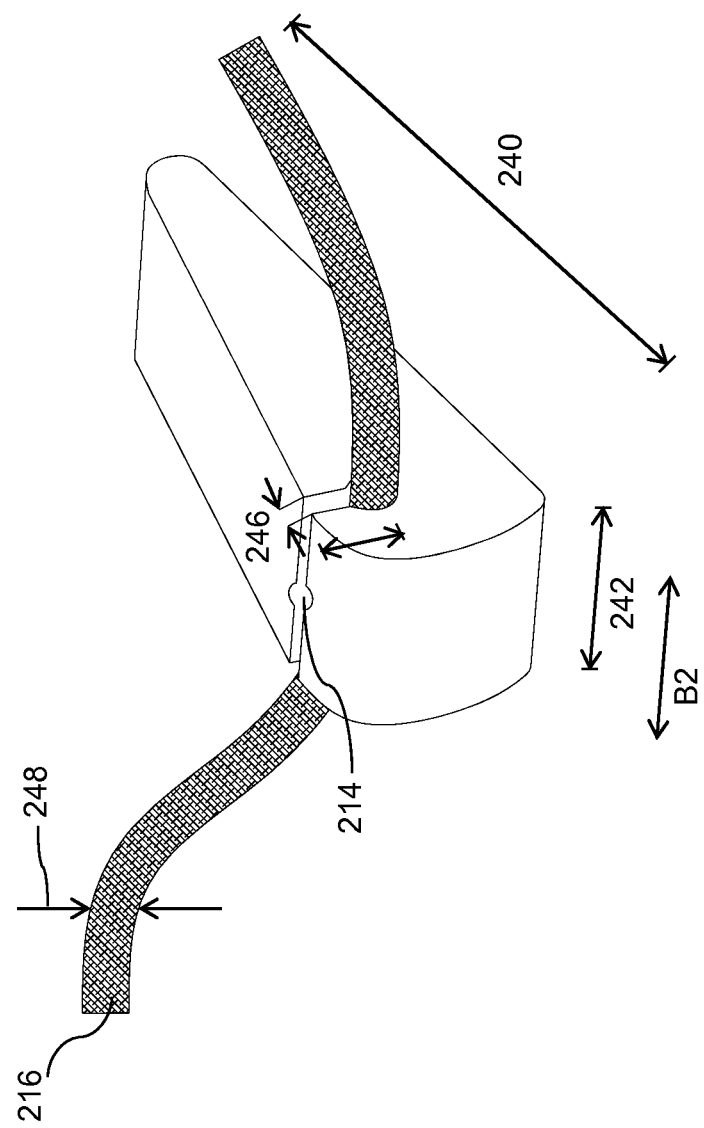
FIG. 2C is a perspective view of a needle receiving portion of the suturing device of FIG. 2A.
Figure 2D:
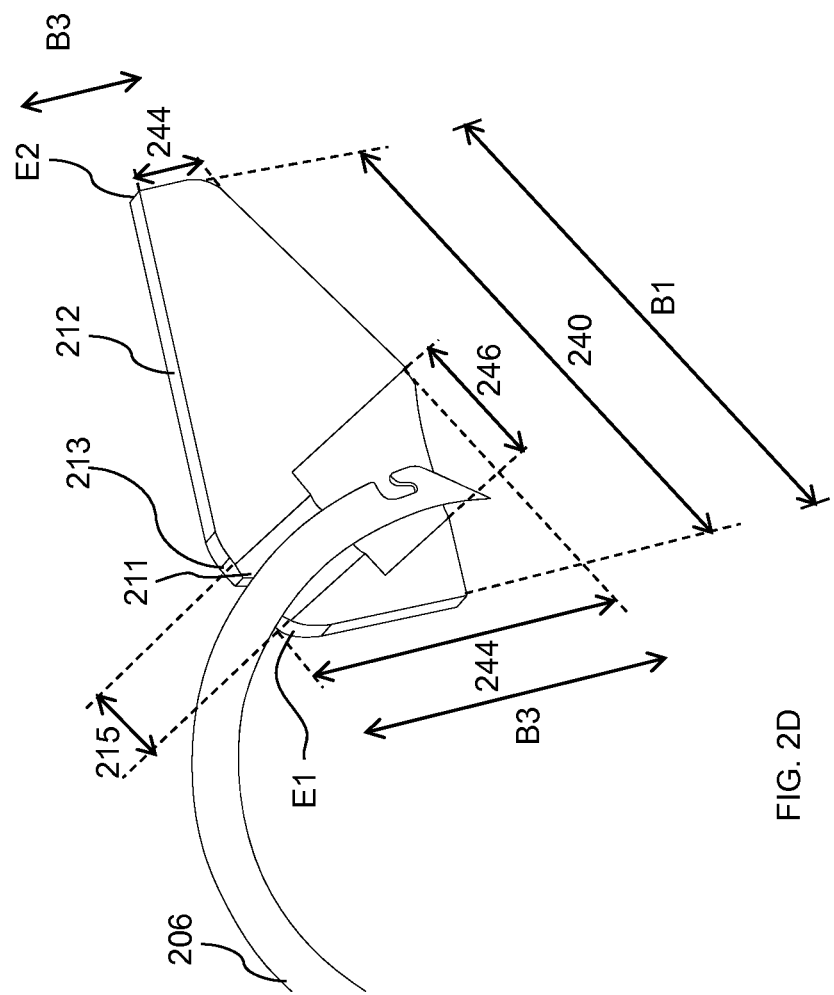
FIG. 2D is a perspective view of the needle receiving portion of the suturing device of FIG. 2A.

FIG. 2C illustrates a perspective view of the needle receiving portion 212 of the elongate member 202 of the suturing device 200. FIG. 2D illustrates a cross-sectional view of the needle receiving portion 212 of the elongate member 202 of the suturing device 200.

Referring now to FIGS. 2A-2D, in accordance with some embodiments of the invention, the needle receiving portion 212 of the suturing device 200 can have a length 240 defined along a direction B1 as shown in FIG. 2D. The length 240 can vary based on the requirements. For example, in some embodiments, the length 240 can vary from 0.30 inch to 0.50 inch. In some embodiments, the length 240 can be 0.40 inch. In some embodiments of the invention, the needle receiving portion 212 can have a width 242 defined along a direction B2 as shown in FIG. 2C. The width 242 can vary based on the requirements. For example, in some embodiments, the width 242 can vary from 0.200 inch to 0.220 inch. In some embodiments, the width 242 can be 0.40 inch.

In some embodiments, the needle receiving portion 212 can have a height 244 defined along two edges E1 and E2 along a direction B3 as illustrated in FIG. 2D. The height 244 of the needle receiving portion 212 can vary based on requirements. In some embodiments, the height of the needle receiving portion 212 can be different across the two edges E1 and E2. For example, in some embodiments, the height along the edge E1 can vary from 0.140 inch to 0.0160 inch and the height along edge E2 can vary from 0.040 inch to 0.060 inch. In some embodiments, the height 244 is 0.150 inch along the edge E1 and 0.050 inch along the edge E2.

The needle receiving portion 212 includes or defines a recess 214. In various embodiments, the recess 214 can be configured to receive a suture 216 and hold it within the recess 214. In some embodiments of the invention, the recess 214 is configured to receive the suture 216 and hold the suture within the recess 214 through frictional or compression fit.

The recess 214 is defined in the form of a slot, an aperture, an opening, or any other type of a hollow space on the needle receiving portion such that the recess is configured to receive the suture and hold the suture within the hollow space provided by the recess 214. In some embodiments, the recess 214 can be, for example, an L-shaped slot or a T-shaped slot. In accordance with several embodiments, the holding force between the suture 216 and the needle receiving portion 212 that is capable of holding the suture within the recess 214 may be generated through various modes. In an embodiment, for example, the required holding force may be generated through a compress fit method of inserting the suture 216 within the recess. In accordance with this embodiment, the recess 214 of the needle receiving portion 212 has a recess width 246 smaller than an outer diameter 248 of the suture 216 as illustrated in FIG. 2C. The recess width 246 of the recess 214 can vary based on requirements. For example the recess width 246 can vary between 0.010 inch to 0.020 inch. In some embodiments an inner surface of the recess 214 can define a substantially circular shape. In these embodiments the diameter of the circular shaped surface of the recess 214 can vary based on requirements. In some embodiments, this diameter can be 0.125 inch. The dimension of the outer diameter 248 can vary based on requirements. For example, the dimension of the outer diameter 248 can vary from 0.013 inch 0.015 inch. In some embodiments, of the invention, the dimension of the outer diameter 248 can be 0.014 inch. This difference in dimension allows the suture 216 to compress fit within the recess 214. In some embodiments, the recess 120 is configured to retain the suture in place via a frictional fit between the suture and the needle receiving portion 118.

In accordance with some embodiments of the invention, the recess 214 includes a hole 211 at a top portion 213 of the recess 214. The hole 211 is defined by a diameter 215 as illustrated in FIG. 2D. The dimension of the diameter 215 can vary based on requirements. For example, the dimension of the diameter 215 can vary from 0.050 inch-0.060 inch. In some embodiments of the invention, the dimension of the diameter 215 can be 0.055 inch.

Figure 2E:
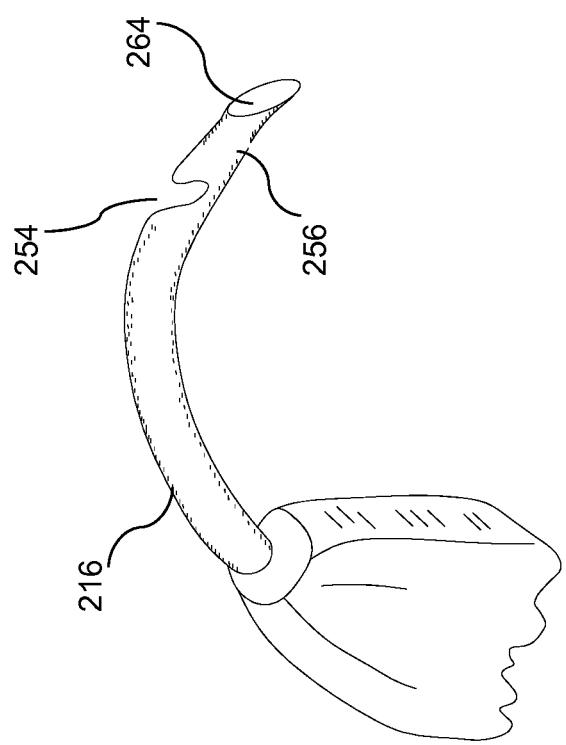
FIG. 2E is a perspective view of a needle with a needle notch, in an embodiment of the present invention.
Figure 2F:
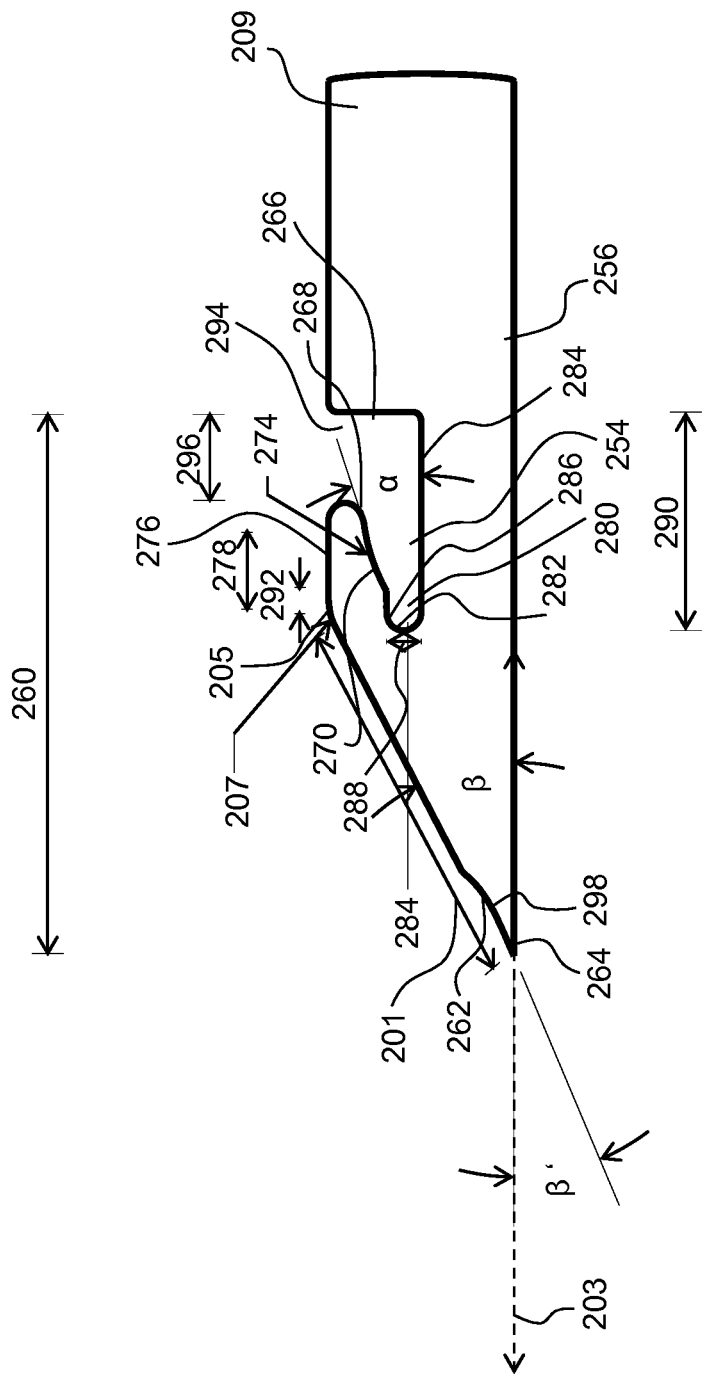
FIG. 2F is a side view of the needle with the needle notch of FIG. 2E.
Figure 2G:
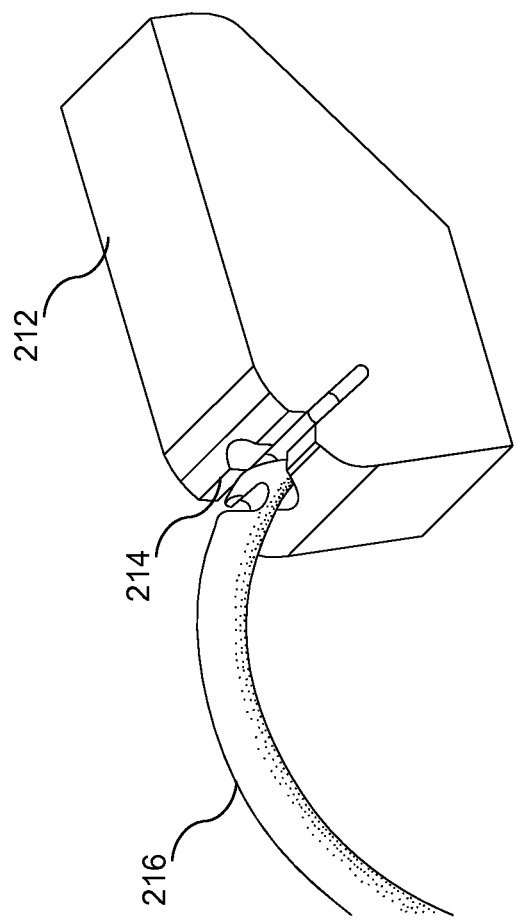
FIG. 2G illustrates a needle and a needle receiving portion of a suturing device.
Figure 2H:
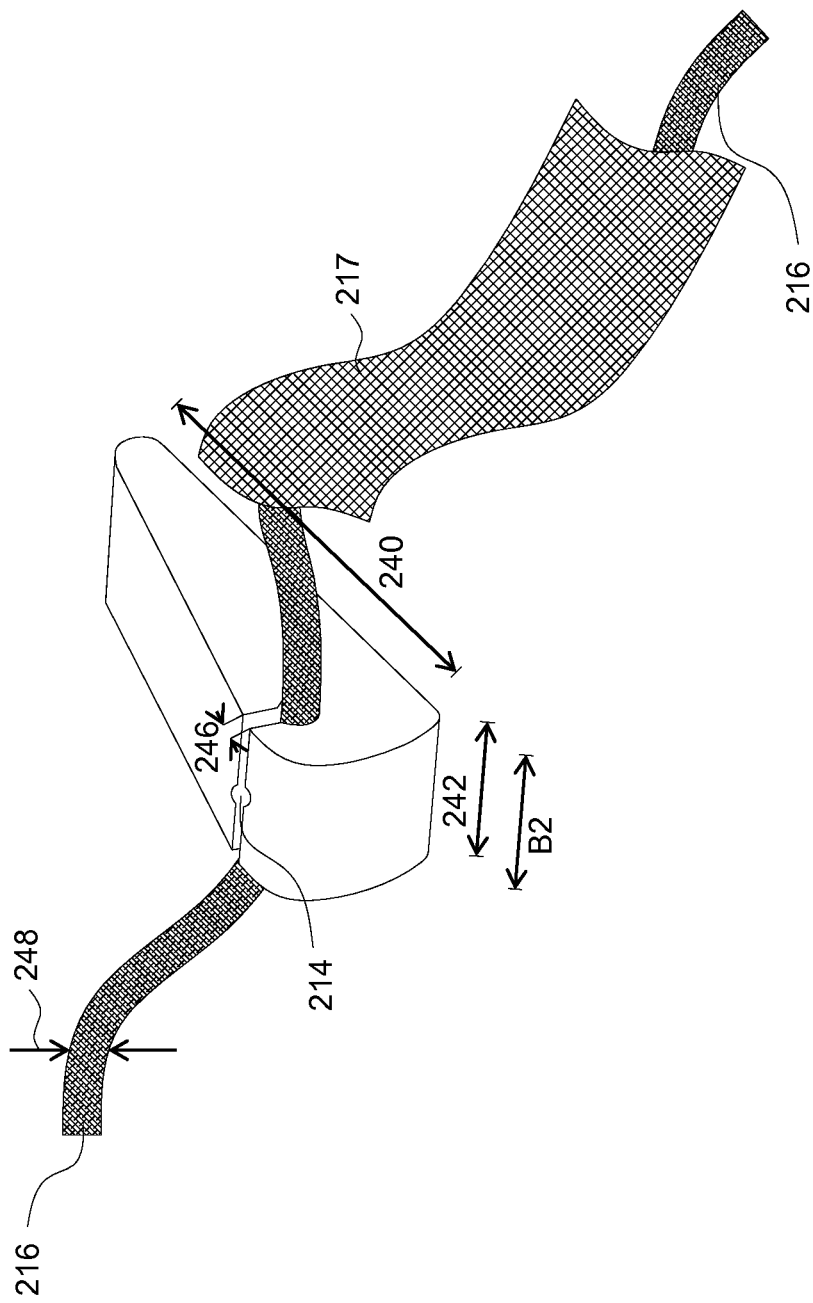
FIG. 2H illustrates a bodily implant coupled to a pair of sutures.
Figure 3A:
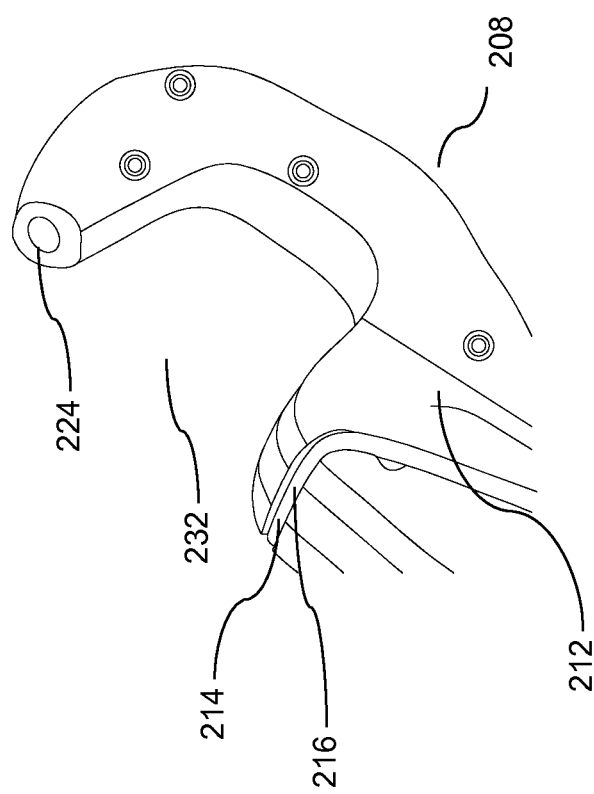
FIGS. 3A-3G illustrate working of a suturing device, in accordance with an embodiment of the present invention.
Figure 3B:
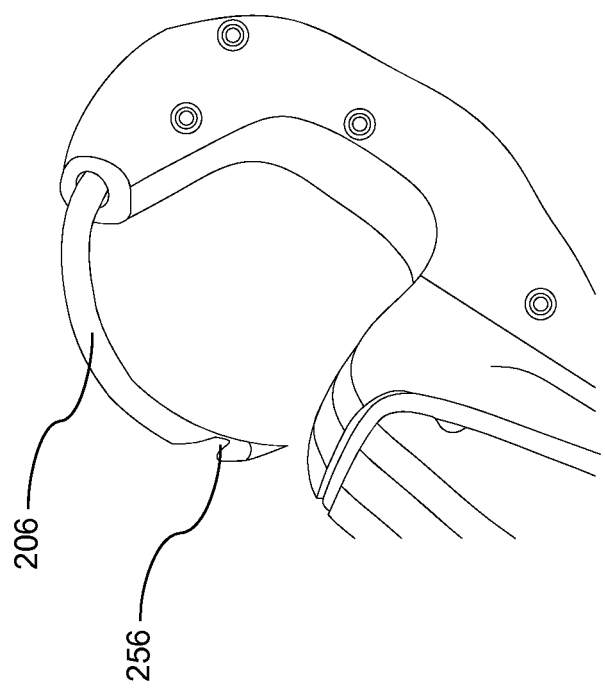
Figure 3C:
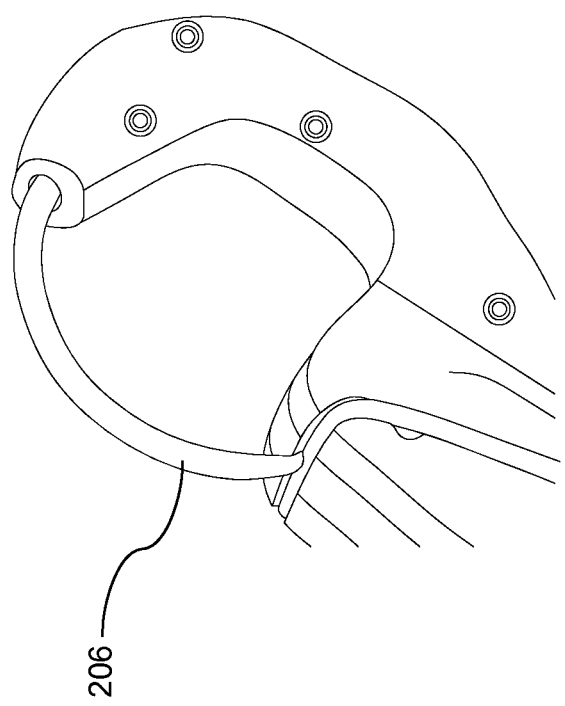
Figure 3D:
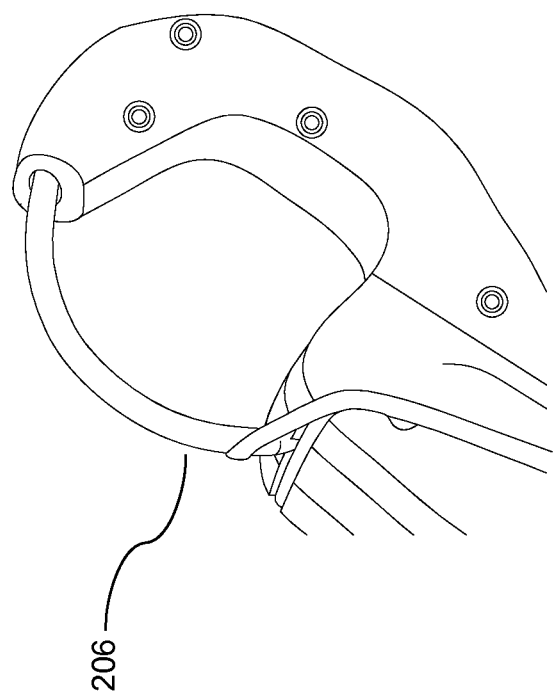
Figure 3E:
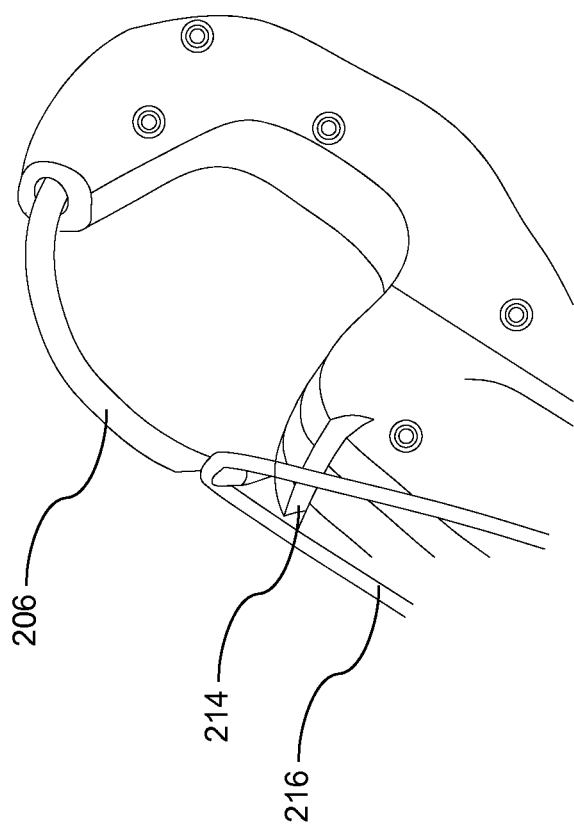
Figure 3F:
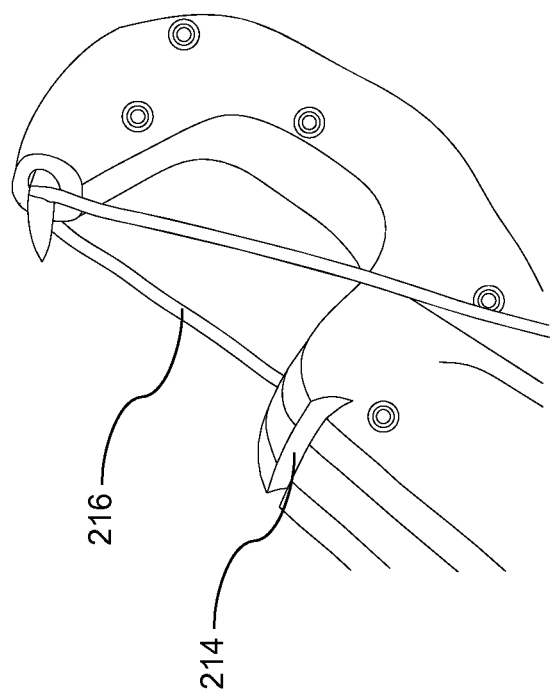
Figure 3G:
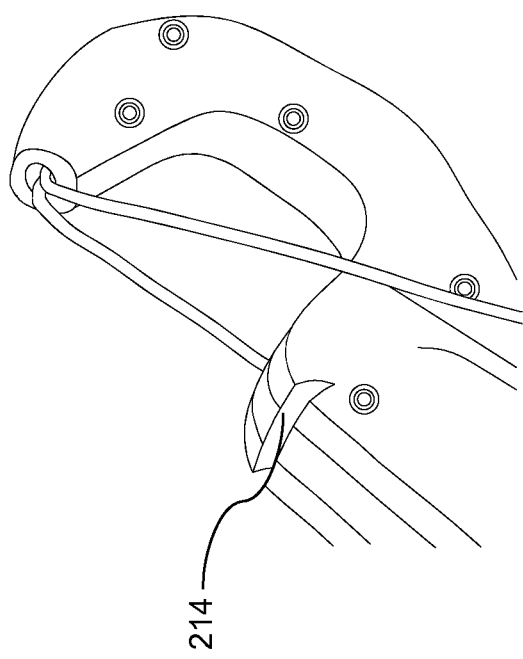

In some embodiments of the invention, at least a portion of an implant 217 (as shown in FIG. 2H) configured to be inserted into a body of a patient can be coupled to the suture 216. In several other embodiments, the holding force can be generated by various modes other than the compress fitting. In some embodiments, the suture 216 can be placed into the recess 214 by applying a push force to the suture 216 so that it compress fits into the recess 214. In such cases, the dimension of the recess 214 and the outer diameter 248 of the suture 216 can be equal or the dimension of the recess 214 can be even more than the outer diameter 248 of the suture 216. In accordance with these embodiments, the suture may be coupled to the recess through various other means that may temporarily hold the suture firmly. In other embodiments, the recess 120 is configured to retain the suture in place via a frictional fit between the suture and the needle receiving portion 118.

In some embodiments, the recess 214 can have a depth referred to as recess depth 250. The recess depth 250 can vary based on requirements. For example the recess depth 250 can vary between 0.080 inch to 0.090 inch. In some embodiments, the recess depth 250 can be 0.082 inch. Referring to FIGS. 2A and 2B, the needle deployment mechanism 204 and the needle 206 are elaborated below.

The needle deployment mechanism 204 is disposed at least partially within the elongate member 202. The needle deployment mechanism 204 is configured to provide either of a deployed state or a retracted state to the suturing device 200. In some embodiments, the needle deployment mechanism 204 is coupled to the elongate member 202 at the tail portion 210. In some embodiments, the needle deployment mechanism 204 is coupled to the elongate member 202 with the help of the bearing 238 as explained above. In several other embodiments, various other mechanical coupling or linkages may be used to couple the needle deployment mechanism 204 with the elongate member 202. In some embodiments, the needle deployment mechanism 204 is at least partially disposed within the lumen 222 of the elongate member 202. In some embodiments, the needle deployment mechanism 204 includes an actuator 252 at least partially disposed within the lumen 222 of the elongate member 202. In some embodiments of the invention, the actuator 252 provides the deployed state and the retracted state to the suturing device 200.

In some embodiments, the actuator 252 can be actuated between the deployed state and the retracted state through a button 236. The button 236 can be provided on the tail portion 210 of the elongate member 202 or on the handle 234 in accordance with different embodiments.

The suturing device 200 can be moved from the retracted state to the deployed state by actuating the needle deployment mechanism 204 along a direction A1 (illustrated in FIG. 2A). After being moved to the deployed state, the needle deployment mechanism 204 can be moved to the retracted state by actuating the needle deployment mechanism 204 along a direction A2 which is opposite to the direction A1. In some embodiments, the needle deployment mechanism 204 is biased towards the retracted state.

The suturing device 200 further includes the needle 206. The needle 206 of the suturing device 200 is partially disposed into the lumen 222 of the elongate member 202 and coupled to a distal portion 258 of the needle deployment mechanism 204 such that the needle 206 moves along the direction in which the needle deployment mechanism 204 is actuated. The needle 206 is configured to exit the lumen 222 in the deployed state and is completely or substantially contained inside the lumen 222 in the retracted state of the suturing device 200.

The needle 206 includes a needle notch 254 at a distal portion 256 of the needle. The needle 206 is configured to enter the recess 214 of the needle receiving portion 212 and receive the suture 216 within the needle notch 254 while in the retracted state.

In some embodiments, the needle 206 can be coupled to the actuator 252 of the needle deployment mechanism 204 at the distal end 258 of the needle deployment mechanism 204. In some embodiments, the distal end 258 of the needle deployment mechanism can be same as a distal end of the actuator 252.

In some embodiments, the needle 206 has a substantially circular cross section. In some embodiments of the invention, the needle 206 is a curved needle. In some other embodiments, the needle 206 can have a different shape. In some embodiments, the needle 206 can have a cross-sectional shape (or outer shape) of any type of polygon. For example, the needle can have a square or a rectangular cross-sectional shape (or outer profile). In some embodiments, the needle 206 can have a tapered shape and/or a tapered portion (e.g., tapered from a proximal portion to a distal portion). In such embodiments, the needle can have a varying diameter or width.

In some embodiments, at least a portion of the needle 206 can be formed of a flexible material. For example, a portion of the needle 206 that remain disposed within the lumen 222 when in the suturing device 200 is in the retracted state can be configured to flex or bend. In some embodiments, at least a portion of the needle 206 that is made of the flexible material can be biased to a specified position and/or curvature. In some embodiments, at least a portion of the needle 206 can be formed of a flexible material so that a portion of the needle can conform to a curvature of the lumen 222 (e.g., a varying curvature), if curved, as the needle 206 is slidably moved within the lumen 222.

FIG. 2E illustrates a perspective view of the needle 206 with the needle notch 254. FIG. 2F illustrates a schematic diagram of the needle 206 with the needle notch 254.

Referring to FIGS. 2E and 2F, a schematic diagram of the distal end 256 of the needle 206 with the needle notch 254 at the distal portion 256 of the needle 206 is shown.

The needle 206 includes the needle notch 254 at the distal portion 256 of the needle 206. In some embodiments of the invention, a length 260 defines a portion of the needle covered by the needle notch 254 and an inclined edge 262 along a longitudinal direction. The length 260 is defined from a tip 264 of the needle to a proximal portion 266 of the needle notch 254. The length 260 can vary based on the requirements. For example, in some embodiments, the length 260 can vary from 0.240 inch to 0.260 inch.

In some embodiments, the needle notch 254 includes a beveled edge 268. The beveled edge 268 is defined by a bevel angle represented by α. The dimension of the bevel angle α can vary based on the requirements. For example, in some embodiments, the bevel angle α can vary from 15 degrees to 30 degrees. In an exemplary embodiment of the invention, the bevel angle α can be 18 degrees.

In some embodiments, the beveled edge 268 can have a circular edge 270. The circular edge 270 defines a radius of curvature 274. The radius of curvature 274 of the circular edge 270 can vary based on the requirements. For example, in some embodiments, the radius of curvature 274 of the circular edge 270 can vary from 0.002 inch to 0.008 inch. In an exemplary embodiment of the invention, the radius of curvature 274 can be 0.006 inch. In some embodiments, the beveled edge 268 includes a linear edge 276 opposite to the circular edge 270. A length 278 defines the length of the linear edge 276. The length 278 can vary based on the requirements. For example, in some embodiments, the length can vary from 0.030 inch to 0.040 inch.

In some embodiments, the circular edge 270 of the needle 206 abuts a pocket 280. The pocket 280 is defined by a wall 282, a floor 284 and a ceiling 286 of the needle notch 254. The wall 282 is defined by a length 288 of the wall 282 which may vary based on requirements. For example, in some embodiments, the length 288 can vary from 0.010 inch to 0.020 inch. In some embodiments, the length 288 can be 0.016 inch. The floor 284 of the needle notch 254 is defined by a floor length 290. The floor length 290 can vary based on the requirements. For example, in some embodiments, the floor length 290 can vary from 0.090 inch to 0.080 inch. In some embodiments, the length 288 can be 0.095 inch. The ceiling 286 of the needle notch 254 is defined by a ceiling length 292. The ceiling length 292 can vary based on the requirements. For example, in some embodiments, the ceiling length 292 can vary from 0.010 inch to 0.020 inch. In some embodiments, the ceiling length 292 can be 0.016 inch.

In some embodiments, the needle notch 254 defines a suture opening 294. The suture opening 294 is defined by a suture opening length 296. The suture opening length 296 can vary based on the requirements. For example, in some embodiments, the suture opening length 296 can vary from 0.030 inch to 0.050 inch. In some embodiments, the suture opening length 296 can be 0.040 inch.

In accordance with some embodiments, the distal portion of the needle includes the inclined edge 262. In some embodiments, the inclined edge 262 has a tapered distal end 298. In some embodiments the inclined edge 262 is defined by a length 201. The length 201 can vary based on the requirements. For example, in some embodiments, the length 201 can vary from 0.145 inch to 0.165 inch. In some embodiments, the length 201 can be 0.155 inch.

In accordance with some embodiments, the inclined edge 262 defines an angle of inclination represented by β. The angle of inclination β is made by the tip 264 of the needle 206 with a horizontal plane 203 of the needle 201. In some embodiments, the angle of inclination β can vary based on requirements. For example, in some embodiments of the invention, the angle of inclination β can be an acute angle varying between 20 degrees to 30 degrees. In some embodiment of the invention, the angle of inclination β can be 26 degrees. As mentioned above, in some embodiments, the inclined edge 262 can have the tapered distal end 298. In this case, there can be a variation in the angle of inclination β and there can be more than one angle of inclination at different portions. In some embodiments, there can be a gradual decrease in the angle of inclination β and the angle of inclination can be denoted by a first angle of inclination β and a second angle of inclination β'. In an exemplary embodiment, the first angle of inclination can be 26 degrees and the second angle of inclination can be 22 degrees.

In some embodiments, the inclined edge 262 abuts into a circular pathway 205 with connects the inclined edge 262 to the linear edge 276. The curved pathway 205 can be defined by a radius of curvature 207. The radius of curvature 207 of the circular edge 205 can vary based on the requirements. For example, in some embodiments, the radius of curvature 207 of the circular pathway 205 can vary from 0.040 inch to 0.060 inch. In some embodiments, the radius of curvature 207 can be 0.050 inch.

In accordance with some embodiments of the invention, when the suturing device 200 is in the retracted state, the distal portion 256 of the needle 206 is disposed within the lumen 222 of the elongate member 202. When the suturing device 200 moves to the deployed state, the distal part 256 of the needle 206 followed by a proximal portion 209 of the needle 206 starts moving out of the lumen 222 toward the recess 214 of the needle receiving portion 212. When the suturing device 200 reaches the deployed state, the needle 206 is completely or substantially extended out of the lumen 222, has pushed through the bodily tissue and entered into the recess 214 of the needle receiving portion 212.

In some embodiments, when the needle 206 is pushed through the bodily tissue, the needle bevel 268 runs into the suture 216 that can be compress-fit into the recess 214 of the needle receiving portion 212. The suture 216 in this case may be stiffer than the needle 206 and this may cause the needle 206 to deflect away, in some embodiments. When the needle notch 254 moves against the suture 216, the needle 206 snaps back and catches the suture 216 into the needle notch 254. The suture 216 is placed onto the floor 284 of the needle notch 254 and the beveled edge 268 of the needle 206 along with the wall 282 of the pocket 280 of the needle notch 254 holds the suture 216 in place. The needle 206 retracts and pulls the suture 216 through the bodily tissues.

The needle notch 254 of the needle 206 picks up the suture 216 from the recess 214 of the needle receiving portion 212 in order to place the suture 216 through the bodily tissues. Also, the suture 216 jammed or compress fitted into the recess 214 of the needle receiving portion 212 can be any kind of suture such as a usually used suture or a customized suture.

In some embodiments, when the suturing device 200 is moved to the deployed state, the needle notch 254 of the needle 206 can be coupled to the suture 216 placed in the recess 214 of the needle receiving portion 212. When the suturing device 200 is moved to the retracted state after needle notch 254 is coupled to the suture 216, the suture 216 can be decoupled from (e.g., extracted from, removed from) the recess 214 of the needle receiving portion 212.

As mentioned above, in some embodiments, the suturing device 200 may be used to insert a suture 216 into a pelvic region of a patient. Specifically, the suturing device 200 can be used to insert a suture 216 into a pelvic region of a patient using an outside-in method.

First, the suture 216 can be coupled to, or associated with, the recess 214 included in the needle receiving portion 212 of the elongate member 202 of the suturing device 200. After the suture 216 has been coupled to, or associated with, the recess 214 of the needle receiving portion 212, the head portion 208 of the elongate member 202 of the suturing device 200 (e.g., at least a portion of the head portion 208 of the elongate member 202) can be inserted into a body of a patient. In some embodiments, the head portion 208 may be inserted into the pelvic region of the patient through an anterior vaginal incision (i.e., via an outside-in approach). In some embodiments, the suturing device 200 can be inserted into the body of the patient such that the head portion 208 of the elongate member 202 is moved along an edge of, or in close proximity to, an edge of a bone (e.g., a pelvic bone) of the patient.

In some embodiments, when the bodily tissues of a patient (e.g., an obturator muscle) is relatively stiff and/or relatively difficult to pierce, the curved portion 230 of the elongate member 202 can function as a support for the needle as the needle notch 254 is moved through the tissue(s). Specifically, structure surrounding the lumen 222 of the elongate member 202 can be made of a relatively rigid material that can prevent (or substantially prevent) the needle 206 from bending in an undesirable fashion. In some embodiments, the structure surrounding the lumen 222 can support the needle 206 while the distal portion 256 of the needle 206 is moved through a tissue so that the needle may not be deformed inelastically.

In some embodiments, the suturing device 200 can be in the retracted state (or moved to the retracted state) when at least the head portion 208 of the elongate member 202 of the suturing device 200 is inserted into the body of the patient.

FIG. 2G illustrates the needle 206 and the needle receiving portion 212 of the suturing device 200 in a different orientation.

FIG. 2H illustrates the implant 217 coupled to the suture 216. The suturing device 200 can be used to place the implant 217 inside the body of a patient. The suture 216 can be placed inside the recess 214 of the needle receiving portion 212 of the suturing device 200. The placement of multiple sutures is described later in conjunction with FIG. 4.

FIGS. 3A-3G illustrates a method of operation of the suturing device 200.

Referring now to FIGS. 3A-3G in conjunction with FIGS. 2A-2E, the method of operation of the suturing device 200 is described in accordance with an embodiment, of the present invention. The suturing device 200 is used for suture 216 placement inside body tissues, for example in a pelvic region of a patient. In some embodiments, the suturing device 200 is employed during the treatment of genital prolapse. The suturing device 200 may be used by the operator as defined above.

In accordance with some embodiments of the invention, when the elongate member 202 of the suturing device 200 is inserted into the body of the patient, the suturing device 200 can be in the retracted state so that the distal end 256 of the needle 206 may not come in contact with the bodily tissue of the patient (because the distal end 256 will be disposed within the lumen 222 of the elongate member 202).

After the elongate member 202 has been inserted into the body of the patient, the suturing device 200 can be moved to the deployed state from the retracted state. Specifically, the needle deployment mechanism 204 can be actuated thereby actuating the needle 206 to move out of the lumen 222 and move toward the recess 214 of the needle receiving portion 212. When moved to the deployed state, the needle 206 of the suturing device 200 may come in contact with the body of the patient.

In some embodiments, the suturing device 200 may be placed in a desirable location with respect to, for example an obturator muscle and/or another target membrane of a patient before being moved to the deployed state. Specifically, the suturing device 200 may be placed so that the suturing device 200 is positioned on either side of the bodily tissue which would be joined. The positioning of the suturing device 200 is such that the bodily tissue to be joined is placed in between the head portion 208 of the elongate member 202 and the needle receiving portion 212 of the elongate member 202. Accordingly, when the suturing device 200 is moved to the deployed state, the distal portion 256 of the needle slidably moves through the lumen 222 of the elongate member 202 and pierces through the bodily tissue (and/or another target membrane) of the patient and moves towards the recess 214 of the needle receiving portion 212.

After the suturing device 200 (e.g., the head portion 208 and the needle receiving portion 212) is in the refracted state in a desirable location around, for example, the bodily tissue (and/or another target membrane) of the patient, the suturing device 200 can be moved from the retracted state to the deployed state (along direction A1) so that the distal portion 256 of the needle 206 can be deployed (e.g., extended out of the lumen 222 of the elongate member 202) and pierced through the obturator muscle (and/or another target membrane). The distal portion 256 of the needle 206 may be moved until the needle notch 254 on the distal portion 256 of the needle contacts and engages to at least a portion of the suture 216 coupled to, or associated with the recess 214 of the needle receiving portion 212.

During a medical procedure, the head portion 208 and the needle receiving portion 212 of the elongate member 202 (and the suture 216 coupled thereto) may not be visible to a physician using the suturing device 200 when the head portion 208 and the needle receiving portion 212 of the elongate member 202 (and the suture 216 coupled thereto) are disposed within the body of the patient. Even though the head portion 208 and the needle receiving portion 212 of the elongate member 202 (and the suture 216 coupled thereto) may not be visible to the physician using the suturing device 200 when the suturing device 200 is moved to the deployed state, the needle 206 may be configured so that the needle notch 254 of the needle 206 may be engaged to at least a portion of the suture 216 in a desirable fashion. In accordance with some embodiments, the suture 216 may be configured (e.g., configured with a stiffness or made of a greater outer diameter 248 than the width 246 of the recess 214 of the needle receiving portion 212) so that the needle notch 254 of the needle 206 is effectively deflected away and slid onto the suture 216 when the needle is brought in contact with the suture 216. This causes the needle notch 254 to come in contact with the suture 216. When the needle notch 254 comes in contact with the suture 216, the needle 206 snaps back and the suture 216 is decoupled from the recess 214 of the needle receiving portion 212 and the suture 216 gets engaged to the needle notch 254 of the needle of the suturing device 200. The suture 216 is placed onto the floor of the needle notch 254 and the beveled edge 268 of the needle 206 along with the wall 282 of the pocket 280 of the needle notch 254 holds the suture 216 in place. The needle 206 can retract and pull the suture 216 through the bodily tissues.

After the needle notch 254 is engaged to the suture 216, the suturing device 200 (needle deployment mechanism 204) can be moved in the direction A2 from the deployed state to the refracted state so that the needle along with the suture 216 may be withdrawn from the bodily tissue. In other words, the needle can be retracted, while coupled to the suture 216 (or at least a portion thereof). Thus, the suture 216 can be extracted from the recess 214 of the needle receiving portion 212 and moved from the recess 214 of the needle receiving portion 212 toward the lumen 222 of the elongate body member along with the needle. The suture 216 along with the needle 206 is moved away from the needle receiving portion 212 and toward the opening of the head portion 208 as the suturing device 100 is moved to the retracted state.

In accordance with the embodiments of the invention, the suture 216 has two ends such that one end is configured to completely pass through the tissues upon retraction and reside on an opposite side. The length of the suture portion that is configured to pass across the tissue to the opposite side may be 8-15 centimeter (8-15 cm), in some embodiments. In some embodiments, this length of the suture portion is at least equal to width of the tissue or opening that is configured to be sutured. In some embodiments, the suture 216 is placed in the recess 214 in such a way that one of the ends of the suture is at a distance of 8-15 centimeter (8-15 cm) from the recess 214 so that the suture 216 leaves suture portions on both sides of the recess 214. The distance of 8-15 cm on one end makes one of the suture portions at one side of the recess shorter than the other. When the needle is refracted back to the lumen 222 of the elongate member 202 of the suturing device 200, the suture portions also get pulled along with the needle into the lumen 222 of the elongate member 202 through the tissues. When the suture 216 is pulled through, the long suture portion is left inside and through the bodily tissue.

Figure 4:
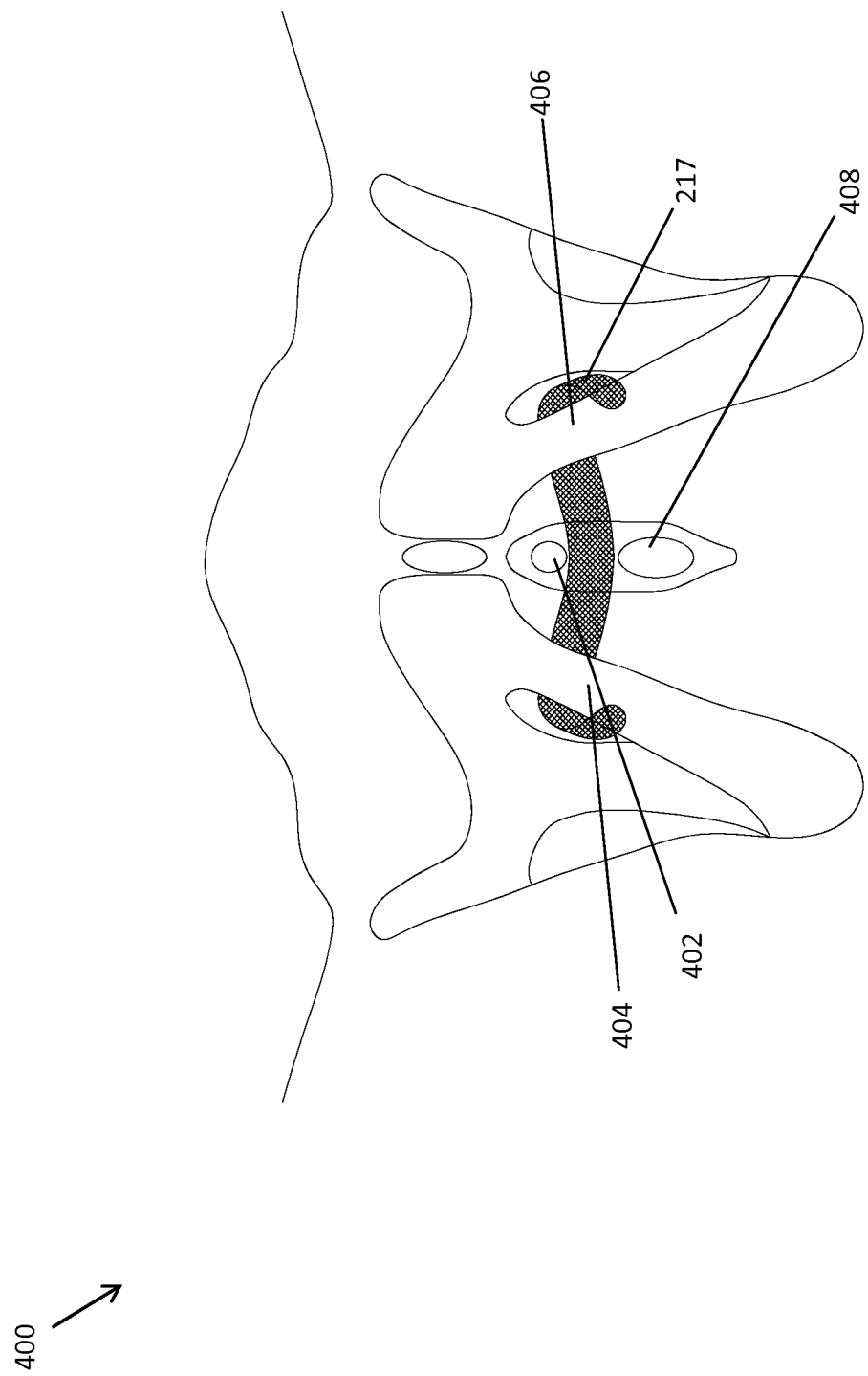
FIG. 4 illustrates a bodily implant being placed inside a pelvic region of a patient.

FIG. 4 illustrates the bodily implant 217 being placed inside the pelvic region of the body of the patient.

FIG. 4 is referred to in conjunction with FIGS. 2A-2H.

Referring now to FIG. 4, a front view of the pelvic region is shown that includes a representation of a urethra 402, a first part of pelvic tissue 404, a second part of the pelvic tissue 406, a vaginal incision 408. In some embodiments, the bodily implant 217 can be secured to the bodily tissue (in this case pelvic tissues 404 and 406) for repair of a genital prolapse that can be delivered using the suturing type delivery device 200 as described above.

FIG. 5 is a flowchart illustrating a method 500 of placement of the suture 216 using a device such as the suturing device 200, in accordance with an embodiment, of the present invention.

Referring now to FIG. 5 in conjunction with FIGS. 2A-2E and FIGS. 3A-3G, the method of placement of the suturing device 200 is described, in accordance with an embodiment of the present invention. The suturing device 200 is hereafter used to describe the placement in an exemplary embodiment; however, it must be appreciated that the suturing device 100 may also be used in a similar manner.

The method includes creating an incision into a patient's body for delivery of the suturing device 200 at step 5502.

In accordance with some embodiments described by method 5500, the suturing device 200 is inserted into the incision at step 504. The suturing device 200 is placed in such a way such that the bodily tissue to be sutured across is positioned in the second opening.

The actuator of the needle deployment mechanism 204 is actuated thereby actuating the suturing device 200 and the suturing device 200 is brought to the deployed state. This causes the needle to move out of the lumen 222 of the elongate member 202 of the suturing device 200 and pass through the bodily tissue and contact the needle receiving portion 212 of the suturing device 200 as in step 506. In some embodiments, actuating can include moving the suturing device 200 in the direction A1 (shown in FIG. 2A). The method can include moving the needle in the direction of A1 along the lumen 222 of the elongate member 202 away from the head portion 208 and toward the needle receiving portion 212 until the needle has moved into the recess 214. In some embodiments, the suture 216 is placed in the recess 214 of the needle receiving portion 212 such that the outer diameter of the suture 216 is larger than the width of the recess 214. This stiffens the suture 216 with respect to the needle 206.

The needle 206 is contacted with the suture 216 that is placed into the recess 214 of the needle receiving portion 212 after the needle has moved into the recess 214. When the distal portion 256 of the needle comes in contact with the suture 216 placed in the recess 214, the needle gets deflected away since the suture 216 is stiffer than the needle, in some embodiments. This may cause the needle to snap back and receive or catch the suture 216 that is fitted into the recess 214 by engaging the suture 216 into the needle notch 254 at step 508. This may cause the suture 216 to be decoupled from the recess 214 and get coupled or engaged to the needle notch 254 of the needle 206. The suturing device 200 (or the needle 206) is then actuated to the retracted state from the deployed state at step 510 such that the needle 206 catches the suture 216 from the recess 214 and pulls it through the tissue.

In accordance with some embodiments of the invention, the needle 206 is brought to the retracted state by actuating the needle deployment mechanism 204.

In some embodiments, a suturing device includes an elongate member, and a needle. The elongate member has a head portion, a tail portion and a needle receiving portion provided on the head portion. The needle receiving portion has a recess. The recess is configured to receive a suture. The needle receiving portion is fixed with respect to an opening defined at the head portion. The needle has a retracted state and a deployed state. The needle includes a needle notch at a distal portion of the needle. The needle is configured to enter the recess of the needle receiving portion and receive the suture within the needle notch.

In some embodiments, the elongate member includes a lumen that extends from the head portion to the tail portion of the elongate member and the elongate member further defines an opening at the head portion. In some embodiments, the suturing device includes a needle deployment mechanism configured to be at least partially disposed within the lumen of the elongate member. In some embodiments, the needle has a substantially circular cross section. In some embodiments, the needle deployment mechanism includes an actuator coupled to the needle. In some embodiments, the needle is at least partially disposed into the lumen in the retracted state. In some embodiments, the needle is configured to at least partially exit the lumen in the deployed position and is completely contained inside the lumen in the retracted position of the suturing device.

In some embodiments, the needle notch includes a beveled edge. In some embodiments, the recess is configured to receive a suture and hold the suture within the recess through compress fit. In some embodiments, the recess of the needle receiving portion has a dimension smaller than an outer diameter of the suture that is configured to allow the suture to compress fit within the recess.

In some embodiments, a suturing device includes an elongate member, a needle deployment mechanism, and a curved needle. The elongate member has a head portion, a tail portion and a needle receiving portion provided on the head portion. The needle receiving portion has a recess. The recess is configured to receive a suture. The needle receiving portion is fixed with respect to an opening defined at the head portion. The elongate member further includes a lumen along a length of the elongate member. The needle deployment mechanism is disposed at least partially within the lumen of the elongate member. The needle deployment mechanism includes an actuator at least partially disposed within the lumen of the elongate member. The curved needle is coupled to the actuator. The curved needle includes a needle notch at a distal portion. The curved needle is configured to at least partially exit the lumen in a deployed position and is completely contained inside the lumen in a retracted position of the suturing device. The distal portion of the curved needle is configured to enter the recess of the needle receiving portion and receive the suture within the needle notch while in a retracted state.

In some embodiments, the recess of the needle receiving portion has a dimension smaller than an outer diameter of the suture that is configured to allow the suture to compress fit within the recess.

In some embodiments, a method for suturing a tissue includes, inserting a suturing device having an elongate member inside a patient's body for suturing the tissue, wherein the suturing device being in a retracted position during insertion; contacting a needle of the suturing device with a needle receiving portion of the suturing device by actuating the suturing device to a deployed position, the needle including a needle notch at a distal portion, wherein the needle receiving portion extends at a head portion of the elongate member, the needle receiving portion being fixed with respect to an opening of the elongate member; receiving a suture from a recess formed at the needle receiving portion; and actuating the suturing device to the retracted position such that the needle catches the suture from the recess and pulls the suture through the tissue.

In some embodiments, the method includes creating an incision in a patient's body for inserting the suturing device.

In some embodiments, the suture is held within the recess through compress fit.

In some embodiments, the receiving of the suture from the recess further comprises engaging the suture into the needle notch.

In some embodiments, the tissue is a tissue from a pelvic region of a body of a patient.

In some embodiments, the method includes closing the incision in the patient's body.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A suturing device comprising:
   an elongate member having a head portion, and a tail portion, the head portion including a needle receiving portion and a tip portion defining an opening, the tip portion being disposed distally from the needle receiving portion, the needle receiving portion defining a recess, the recess of the needle receiving portion defining a first recess portion and a second recess portion, the first recess portion having a width larger than a width of the second recess portion;
   a suture configured to be disposed within the recess, the width of the second recess portion of the needle receiving portion being smaller than an outer diameter of the suture such that suture compress fits within the recess; and
   a needle having a retracted state and a deployed state, the needle having a curved portion, wherein the curved portion of the needle includes a needle notch at a distal portion of the needle, the needle being configured to exit out of the opening on the tip portion and enter the first recess portion of the needle receiving portion and receive the suture within the needle notch.

2. The suturing device of claim 1, wherein the elongate member includes a lumen extending from the head portion to the tail portion of the elongate member.

3. The suturing device of claim 2, wherein the needle is at least partially disposed into the lumen in the retracted state.

4. The suturing device of claim 3, wherein the needle is configured to at least partially exit the lumen in the deployed position and is completely contained inside the lumen in the retracted position of the suturing device.

5. The suturing device of claim 2, further comprising a needle deployment mechanism configured to be at least partially disposed within the lumen of the elongate member.

6. The suturing device of claim 5, wherein the needle deployment mechanism includes an actuator coupled to the needle.

7. The suturing device of claim 1, wherein the needle has a substantially circular cross section.

8. The suturing device of claim 1, wherein the needle notch includes a beveled edge.

9. The suturing device of claim 1, wherein the width of the first recess portion is larger than an outer diameter of the curved portion of the needle.

10. A suturing device comprising:
    an elongate member having a head portion, and a tail portion, the head portion including a needle receiving portion and a tip portion defining an opening, the tip portion being disposed distally from the needle receiving portion, the needle receiving portion defining a first lateral edge and a second lateral edge, the needle receiving portion defining a recess, the recess having a length that extends from the first lateral edge and the second lateral edge and a depth that extends into the needle receiving portion,
    the recess including a first recess portion and a second recess portion, the second recess portion extending from the first lateral edge and the second lateral edge, the first recess portion being disposed at a location between the first lateral edge and the second lateral edge, the first recess portion having a width larger than a width of the second recess portion, the first recess portion being partially defined by the second recess portion, the elongate member further including a lumen along a length of the elongate member;

a needle deployment mechanism disposed at least partially within the lumen of the elongate member, the needle deployment mechanism including an actuator at least partially disposed within the lumen of the elongate member;

a needle coupled to the actuator, wherein the needle includes a curved portion defining a needle notch at a distal portion of the curved portion, the curved portion of the needle configured to at least partially exit the lumen in a deployed position and is completely contained inside the lumen in a retracted position of the suturing device; and a suture configured to be disposed within the recess, the width of the second recess portion being smaller than an outer diameter of the suture such that suture compress fits within the recess, wherein the curved portion of the needle is configured to exit out of the opening on the tip portion and enter the first recess portion of the needle receiving portion and receive the suture within the needle notch while in a retracted state.

11. A suturing device comprising:

an elongate member including a head portion, the head portion defining a needle receiving portion and a tip portion defining an opening, the tip portion being disposed distally from the needle receiving portion, the needle receiving portion defining a first lateral edge and a second lateral edge, the needle receiving portion defining a recess, the recess having a length that extends from the first lateral edge and the second lateral edge and a depth that extends into the needle receiving portion, the recess including a first recess portion and a second recess portion, the second recess portion extending from the first lateral edge to the second lateral edge, the first recess portion being disposed between the first lateral edge and the second lateral edge at a location along the length of the recess, the first recess portion having a width larger than a width of the second recess portion;

a needle deployment mechanism at least partially disposed within the elongate member;

a suture configured to be disposed within the recess, the width of the second recess portion being smaller than an outer diameter of the suture such that suture compress fits within the recess; and a needle having a retracted state and a deployed state, wherein the needle includes a needle notch at a distal portion of the needle, the needle being configured to exit out of the opening on the tip portion and enter the first recess portion and receive the suture within the needle notch.

12. The suturing device of claim 11, wherein the width of the second recess portion is between 0.010 inch to 0.020 inch.

13. The suturing device of claim 11, wherein the needle notch includes a beveled edge.

14. The suturing device of claim 11, wherein the first recess portion is substantially circular, and has a depth that is same as a depth of the second recess portion.

15. The suturing device of claim 11, wherein the first recess portion is disposed along a longitudinal axis of the head portion.

* * * * *